United States Patent [19]

Forgach

[11] Patent Number: 5,304,129
[45] Date of Patent: Apr. 19, 1994

[54] PIVOTABLE FOOT OPERATED BREAST PUMP

[76] Inventor: Suzanne E. Forgach, 8621 E. Mabel Pl., Tucson, Ariz. 85715

[21] Appl. No.: 89,498

[22] Filed: Jul. 12, 1993

[51] Int. Cl.⁵ ............................................. A61M 1/06
[52] U.S. Cl. ..................................... 604/74; 417/473
[58] Field of Search .......... 604/74, 118, 119, 313–315; 417/472, 473; 119/14.24

[56] References Cited

U.S. PATENT DOCUMENTS

| | | | |
|---|---|---|---|
| 11,135 | 6/1854 | Needham | 604/74 |
| 1,056,865 | 3/1913 | Webster | 417/473 |
| 4,187,845 | 2/1980 | Dror | 128/205.13 |
| 4,680,028 | 7/1987 | Stuart | 604/74 |
| 4,892,517 | 1/1990 | Yuan et al. | 604/74 |

Primary Examiner—Jerome L. Kruter
Attorney, Agent, or Firm—Cahill, Sutton & Thomas

[57] ABSTRACT

A breast pump includes a platform resting on the floor or other support and a treadle having a convex surface resting on the platform, permitting a pivoting or seesaw motion of the treadle. A bellows is connected between the treadle and the platform, forming a variable displacement chamber. A flexible hose connects the chamber to a reservoir including a container, such as a baby bottle, and an adaptor attached to the bottle as a cap. There is no valve controlling the flow of air to or from the reservoir, thereby providing complete and precise control of the pressure in the reservoir.

12 Claims, 1 Drawing Sheet

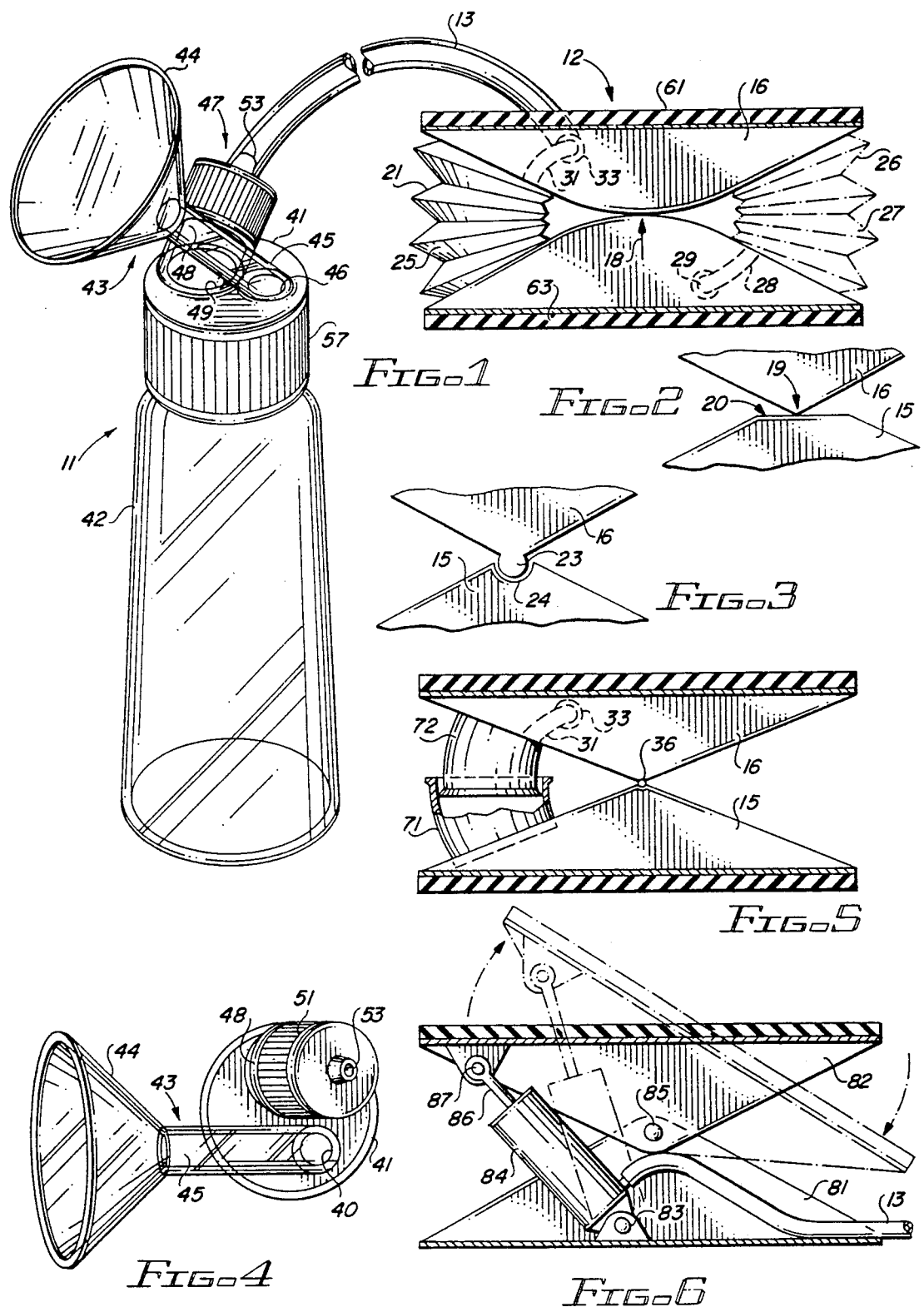

5,304,129

PIVOTABLE FOOT OPERATED BREAST PUMP

BACKGROUND OF THE INVENTION

This invention relates to breast pumps and, in particular, to a foot operated breast pump having a pivoting treadle for providing full control of both halves of the pumping cycle.

In the ideal situation where a mother and baby are together most of the time and the baby is able to nurse on demand, there is little need for a breast pump. However, there are many circumstances which make nursing difficult or impossible and a breast pump is necessary to furnish the baby with the mother's milk; for example, a premature infant who cannot be nursed or a mother returning to work shortly after giving birth. The book, "*The Womanly Art of Breastfeeding*", published by La Leche League International describes several types of manual and electric breast pumps which have been used by women to enhance or facilitate nursing.

A manual breast pump is awkward because it requires both hands to operate, preventing the mother from pumping both breasts simultaneously, holding a baby, or even holding a book to read during the tedious pumping process. Some pumps are designed for single handed operation but require exceptional strength in the fingers to maintain a rhythmic squeezing action. In addition, a single handed breast pump typically requires that the hand performing the rhythmic, strength-intensive pumping also keep the funnel in place on the breast.

Electrically powered breast pumps are a little better, not requiring so much work from one hand, but are more expensive, noisy, less portable, and have less control of suction and rhythm. Many electrically powered breast pumps are so expensive that they are rented rather than purchased. Since a table-top electric breast pump is often the same size as a small sewing machine, a mother cannot always carry the pump with her, requiring that she be at a certain place at a certain time, several times a day, in order to be able to pump the milk her baby needs. Even if the pump is transportable, the mother must find an electrical outlet in a private area, often a difficult task in offices and other public places.

The noise of a motor can compromise privacy even behind a closed door and may be distracting for the mother. Battery powered breast pumps are usually noisy, producing a buzz like an electric razor. Even if a mother is able to resolve the privacy and distraction issues for herself, the baby may be distracted or upset when nursing on one breast while the mother pumps the other breast, as many women do to aid their milk let-down reflex, On an electric breast pump, the controls for suction and rhythm are not as immediate as the quick adjustment provided by a manual breast pump, i.e. suction decreases as soon as the woman slows or stops pumping manually. The controls for suction and rhythm on a battery powered breast pump may be more convenient than the controls on an AC powered breast pump but they are not immediately effective. On some battery powered pumps, suction is controlled by placing a finger over an air hole, an imprecise method which causes the suction to be inconsistent, with possibly painful consequences.

A battery powered breast pump has a further disadvantage in that the woman must always have fresh batteries and spare batteries with her.

In the prior art, U.S. Pat. No. 11,135 by O. H. Needham (1854), describes a manual bellows connected by a flexible hose to a funnel which fits over the breast. This pump requires two hands to operate, one hand for the pump and one hand for the funnel. There is no mechanism in the pump for returning the bellows to a start position and the narrow grip for operating the bellows precludes operation by foot.

In view of the foregoing, it is therefore an object of the invention to provide a manual breast pump requiring only one hand to operate.

Another object of the invention is to provide a breast pump which is portable, quiet, and inexpensive.

A further object of the invention is to provide a manual breast pump which permits control of both halves of the pump cycle.

Another object of the invention is to provide a breast pump requiring little, if any, manual dexterity.

SUMMARY OF THE INVENTION

The foregoing objects are achieved in the invention in which a foot operated, valveless, bellows pump evacuates a reservoir, drawing milk from the mother. The pump includes a small platform resting on the floor or other support and a treadle having a convex surface resting on the platform, permitting a rocking, pivoting, or see saw motion of the treadle. A bellows is connected between the treadle and the platform, forming a variable displacement chamber. A flexible hose connects the chamber to the reservoir. As the chamber increases in volume, the pressure in the chamber decreases, decreasing the pressure in the reservoir and drawing milk into the reservoir. The reservoir preferably includes a standard baby bottle and an adapter attached to the bottle as a cap. The adapter has a first fitting to which the flexible hose is attached and a second fitting including a flare or funnel for placing on a woman's breast. The fittings are separated to assure that milk flows into the bottle and not into the hose. The treadle enables comfortable operation by foot which controls both the downstroke and the upstroke of the treadle, giving complete and precise control of the pressure in the reservoir.

BRIEF DESCRIPTION OF THE DRAWINGS

A more complete understanding of the invention can be obtained by considering the following detailed description in conjunction with the accompanying drawings, in which:

FIG. 1 illustrates a breast pump constructed in accordance with the invention in which a bellows is used as the pump mechanism;

FIG. 2 illustrates an alternative contact between the platform and the treadle in FIG. 1;

FIG. 3 illustrates a joint connecting a treadle and a platform;

FIG. 4 is a top view of an adapter connected to a baby bottle;

FIG. 5 illustrates an alternative embodiment of a breast pump constructed in accordance with the invention in which telescoping tubes are used as the pump mechanism; and FIG. 6 illustrates an alternative embodiment of a breast pump constructed in accordance with the invention in which a piston in a cylinder is used as the pump mechanism.

DETAILED DESCRIPTION OF THE INVENTION

FIG. 1 illustrates a breast pump constructed in accordance with a preferred embodiment of the invention in which reservoir 11 is connected to pump 12 by flexible hose 13. Pump 12 includes platform 15 having a convex upper surface and treadle 16 having a convex lower surface. The convex surfaces of platform 15 and treadle 16 touch along a line of contact perpendicular to the plane of the drawing, indicated by reference number 18. The radii of curvature of the convex surfaces are not critical and provide a rocking action of treadle 16 on platform 15 in which line of contact 18 moves left or right as the treadle rocks.

If the radius of curvature of the lower surface of treadle 16 becomes vanishingly small, one obtains corner 19, as illustrated in FIG. 2. If treadle 16 includes corner 19, then platform 15 preferably includes flat 20, i.e. a contact surface having a large radius of curvature. In this configuration, treadle 16 does not rock but pivots on platform 15 and line of contact 18 does not move left or right.

Since a corner contact is subject to high stress and high wear, it is preferred that a pivoting contact include some type of joint to provide a large contact area. FIG. 3 illustrates a bead and cove joint which can be used for the contact between treadle 16 and platform 15 in which bead 23 on the treadle fits in cove 24 on the platform. Other joints, such as a hinge, can be used instead. As shown in FIG. 1, convex surfaces having a moderate radius of curvature are preferred since the platform and treadle can be made easily and inexpensively for this configuration.

In a preferred embodiment of the invention, platform 15 and treadle 16 are elongated blocks of wood having an overall length of approximately twelve inches and a width of approximately four inches. The blocks are two to three inches thick and shaped as shown in FIG. 1.

Bellows 21 is attached between platform 15 and treadle 16, enclosing a variable displacement chamber. Bellows 21 is attached to platform 15 and treadle 16 by any suitable means, such as staples or adhesive. Bellows 21 is preferably connected with an airtight seal since the connection between the pump and the reservoir is unobstructed, as explained below.

Chamber 25 is connected to hose 13 by a pair of intersecting holes in treadle 16. Hole 31 extends from the convex surface into the body of treadle 16 and ends before intersecting the upper surface of treadle 16. Hole 33 is approximately perpendicular to hole 31 and extends through one side of treadle 16 to hole 31. Hose 13 is inserted into hole 33.

Since the mating surfaces of platform 15 and treadle 16 are convex, the treadle rocks on the platform, changing the volume of chamber 25. As the volume of chamber 25 increases, air is drawn through hose 13 from reservoir 11. As chamber 25 decreases in volume, air is supplied to reservoir 11 by hose 13. Unlike bellows for a fireplace, it is preferred that the connection between chamber 25 and reservoir 11 be unobstructed i.e. that there be no valve for controlling air flow, thereby providing a bidirectional pump. The absence of a valve simplifies the construction of the breast pump and provides better control of the pressure within the reservoir. The improved control is compromised if bellows 21 is not sealed to the platform and to the treadle.

Reservoir 11 includes cap 41 and bottle 42. Referring to FIGS. 1 and 4, cap 41 includes fitting 43 for coupling the reservoir to a woman's breast. Fitting 43 includes funnel shaped member 44 and tube 45. Tube 45 is attached to cap 41 around hole 46. Cap 41 includes cylindrical side wall 57 having an internal thread for engaging the threaded end of bottle 42. Preferably, bottle 42 is a standard baby bottle.

The connection to hose 13 is made through a separate hole to assure that milk flows into the reservoir and not into hose 13. Specifically, fitting 47 includes tube 48 having one end enclosing hole 49 and the other end enclosed by cap 51. Cap 51 can be screwed or glued onto tube 48 and includes nipple 53 for receiving hose 13.

As the pressure in reservoir 11 is reduced from atmospheric pressure to a partial vacuum, milk is withdrawn from the breast and flows into bottle 42. The pressure within bottle 42 is fully controllable by the woman, who positions treadle 16 relative to platform 15. Fitting 43 is readily released from the breast by simply increasing the pressure within reservoir 11, i.e. by decreasing the size of chamber 25. The absence of a valve in the connection between chamber 25 and reservoir 11 is not a disadvantage as the reservoir fills with milk since fitting 43 is frequently removed from the breast, e.g. as the woman changes sides during the pumping session.

Either or both of platform 15 and treadle 16 can include a non skid surface such as a rubber layer or a roughened coating. As illustrated in FIG. 1, treadle 16 includes non-skid layer 61 on the upper surface thereof and platform 15 includes non skid layer 63 on the lower surface thereof. Thus, a breast pump constructed in accordance with the invention can be used anywhere, e.g. in a car, at a camp site, at home, or at the office. The operation of the pump is silent and completely controlled by the woman.

Since pump 12 is symmetrical from end to end, a second bellows can be added for pumping both breasts. Bellows 26, on the opposite end of pump 12 from bellows 21, is sealed between treadle 16 and platform 15, enclosing a second variable displacement chamber. Chamber 27 is connected by holes 28 and 29 to a second reservoir (not shown). Bellows 21 and 26 operate oppositely, that is, one bellows increases pressure in a reservoir while the other bellows decreases pressure in the other reservoir.

FIG. 5 illustrates an alternative embodiment of a variable displacement chamber in which concentric, telescoping tubes 71 and 72 are attached between platform 15 and treadle 16. The interior volume of the tubes is coupled by hole 31 and hole 33 to hose 13. Tube 72 is sealed within tube 71 by any suitable means, such as lip 74. Alternatively, a separate gasket could be used between tube 72 and tube 71. In use, the pivoting motion of treadle 16 changes the interior volume of the telescoping tubes. Tubes 71 and 72 are curved slightly to accommodate the motion of treadle 16 about pivot 36. Pivot 36 can be a hinge, a bead and cove joint, or other connection permitting a pivoting motion.

FIG. 6 illustrates another alternative embodiment of the invention in which a cylinder containing a movable piston is used as the variable displacement chamber. In this embodiment, platform 81 and treadle 82 are preferably made from sheet stock and each have a rectangular central portion and two, triangle shaped sides bent at approximately ninety degrees to the central portion. The peaks of the triangles of the sides are interconnected by a hinge such as hinge 85 to provide the pivoting motion for treadle 82. Cylinder 84 is connected to the central portion of platform 81 by hinge 83. A piston (not shown) within cylinder 84 is connected by connecting rod 86 to hinge 87 and hinge 87 is connected to treadle 82.

In operation, the pivoting motion of the treadle moves the piston in cylinder 84, directly changing the pressure within the reservoir. As with the others embodiments, it is preferred that a valve not be used with cylinder 84 to control the flow of air to or from cylinder 84. If a valve were used, the woman can only release the vacuum by depressing the breast within fitting 43 to allow air to enter reservoir 11.

The invention thus provides a manual breast pump requiring only one hand to operate and which permits control of both parts of the pump cycle, vacuum and increased pressure. The breast pump is portable, quiet, and inexpensive. In addition, the pump is inherently safe and does not require additional sensors or valves, e.g. a woman will stop pumping if she falls asleep during a pumping session.

Having thus described the invention, it will be apparent to those of skill in the art that various modifications can be made within the scope of the invention. For example, the pump can be constructed of any suitable material including wood, metal, and/or plastic. The treadle and platform can be hollow or solid. The mating surfaces of platform 15 and treadle 16 can have any suitable shape permitting a pivoting motion of the treadle and the platform and treadle are interchangeable. The special cap for the bottle can be a single piece of molded plastic or several pieces joined together. Hose 13 can be connected to a single, straight hole extending from the convex surface through the upper surface of treadle 16. Alternatively, the connecting hole can be in platform 15. While intended to be operated by foot, a handicapped person can operate the pump by pushing on either end of the treadle with a hand or by resting a forearm on the treadle. Manual dexterity (small motor control) is not required.

I claim:

1. A foot operated breast pump comprising:
   (a) a reservoir including a first fitting for placement on a woman's breast and a second fitting for attachment to a source of vacuum;
   (b) a bi-directional pump including
      (i) a platform,
      (ii) a treadle resting on said platform, and
      (iii) a variable displacement chamber connected between said treadle and said platform;
   (c) a hose connecting said chamber to said second fitting; and
   wherein motion of said treadle in a first direction relative to said platform causes said chamber to increase in volume and decrease the pressure in said reservoir, and motion of said treadle in a second direction relative to said platform causes said chamber to decrease in volume and increase the pressure in said reservoir.

2. The foot operated breast pump as set forth in claim 1 wherein said chamber includes telescoping tubes connected between said treadle and said platform.

3. The foot operated breast pump as set forth in claim 2 wherein said tubes are curved.

4. The foot operated breast pump as set forth in claim 1 wherein said chamber includes a cylinder connected to one of said treadle and said platform and a movable piston in said cylinder, wherein said piston is connected to the other of said treadle and said platform.

5. The foot operated breast pump as set forth in claim 1 wherein said reservoir comprises:
   a cap having an internally threaded, cylindrical sidewall, wherein said first fitting and said second fitting are attached to said cap; and
   a container having an externally threaded end portion which can be screwed into said cap.

6. The foot operated breast pump as set forth in claim 1 wherein said treadle has a convex surface resting on said platform.

7. The foot operated breast pump as set forth in claim 6 wherein said chamber includes a bellows connected between said treadle and said platform.

8. The foot operated breast pump as set forth in claim 6 wherein said platform has a convex surface on which said platform rests.

9. A foot operated breast pump comprising:
   a reservoir including a first fitting for placement on a woman's breast and a second fitting;
   a bidirectional pump for increasing or decreasing the pressure within said reservoir;
   a hose connecting said pump to said second fitting; and
   wherein the connection between the chamber and the reservoir is unobstructed and said reservoir can be pressurized or evacuated by operation of said pump.

10. The foot operated breast pump as set forth in claim 9, wherein
    said bidirectional pump includes:
       (i) a platform,
       (ii) a treadle having a convex surface resting on said platform, and
       (iii) a variable displacement chamber connected between said treadle and said platform;
    and
    said hose connects said chamber to said second fitting.

11. The foot operated breast pump as set forth in claim 10 wherein said treadle rocks on said platform.

12. The foot operated breast pump as set forth in claim 10 wherein said treadle pivots on said platform.

* * * * *

UNITED STATES PATENT AND TRADEMARK OFFICE
CERTIFICATE OF CORRECTION

PATENT NO. : 5,304,129
DATED : April 19, 1994
INVENTOR(S) : Suzanne E. Forgach

It is certified that error appears in the above-identified patent and that said Letters Patent is hereby corrected as shown below:

Column 6, line 37 (Claim 9, line 8, ), change "chamber" to --pump--.

Signed and Sealed this

Twelfth Day of August, 1997

Attest:

BRUCE LEHMAN

Attesting Officer

Commissioner of Patents and Trademarks